United States Patent
Bauer

(12) 
(10) Patent No.: US 6,918,914 B2
(45) Date of Patent: Jul. 19, 2005

(54) MINIMALLY INVASIVE ADJUSTABLE ACETUBULAR REAMER

(76) Inventor: Clayton T. Bauer, 3355 Black Bear Trail, Deland, FL (US) 32724

( * ) Notice: Subject to any disclaimer, the term of this patent is extended or adjusted under 35 U.S.C. 154(b) by 61 days.

(21) Appl. No.: 10/617,063

(22) Filed: Jul. 10, 2003

(65) Prior Publication Data

US 2004/0073224 A1 Apr. 15, 2004

Related U.S. Application Data

(60) Provisional application No. 60/417,571, filed on Oct. 10, 2002.

(51) Int. Cl.[7] .............................................. A61B 17/56
(52) U.S. Cl. ...................................................... 606/81
(58) Field of Search .............................. 606/79, 80, 81

(56) References Cited

U.S. PATENT DOCUMENTS

| | | | |
|---|---|---|---|
| 3,702,611 A | * 11/1972 | Fishbein | ....................... 606/81 |
| 4,611,587 A | * 9/1986 | Powlan | ......................... 606/81 |
| 5,192,291 A | 3/1993 | Pannek, Jr. | |
| 5,236,433 A | * 8/1993 | Salyer | .......................... 606/91 |
| 5,299,893 A | 4/1994 | Salyer et al. | |
| 5,980,170 A | * 11/1999 | Salyer | ..................... 408/239 R |
| 6,283,971 B1 | 9/2001 | Temeles | |
| 6,383,188 B2 | * 5/2002 | Kuslich et al. | ................ 606/80 |
| 6,589,281 B2 | * 7/2003 | Hyde, Jr. | .................. 623/18.11 |
| 6,755,865 B2 | * 6/2004 | Tarabishy | ................. 623/22.12 |

* cited by examiner

Primary Examiner—Eduardo C. Robert
Assistant Examiner—Annette Reimers
(74) Attorney, Agent, or Firm—James H. Beusse; Beusse Brownlee Wolter Mora & Maire, P.A.

(57) ABSTRACT

An acetabular reamer including a reaming head having arcuately-shaped segments generally symmetrically distributed about a center point. The arcuately-shaped segments are extendable or retractable about the center point to create a variable dimensioned recess in an acetabular region. The reamer may also include an actuator for selectively extending or retracting the segments so that the segments remain generally symmetrically distributed about the center point as the segments are expanded or retracted. The segments may further include cutting surfaces having a shape corresponding to a portion of a surface of a hemisphere. In one form, the segments may be configured in a narrow symmetrical "slice" of a hemispherical surface that provides an adjustable hemispherically shaped cutting arc.

11 Claims, 3 Drawing Sheets

US 6,918,914 B2

MINIMALLY INVASIVE ADJUSTABLE ACETUBULAR REAMER

SPECIFIC DATA RELATED TO THE INVENTION

This application claims the benefit of U.S. Provisional Application No. 60/417,571 filed Oct. 10, 2002, incorporated herein by reference.

FIELD OF THE INVENTION

The present invention relates to surgical instruments and, in particular to acetabular reamers.

BACKGROUND OF THE INVENTION

An acetabular reamer having a reamer head is used in hip replacement surgery for reforming the hip socket, or acetabulum, in preparation for implanting a prosthetic component, such as an acetabular cup or socket. To ensure a proper fit of the prosthetic device, deteriorated or diseased bone needs to be cut or shaved away to healthy bone tissue so that the reamed acetabulum matches the contours of the prosthetic to be fitted. In a typical hip replacement procedure including an acetabular implant, a surgeon makes an incision in the hip area, displaces the existing hip joint, shapes the acetabulum with the reamer to receive a metallic or plastic prosthetic socket, inserts the prosthetic socket, replaces the ball of the femur with prosthetic ball, and inserts the prosthetic ball into the prosthetic socket to complete the operation. Typically, removable reamer heads of increasingly larger size are used to enlarge the acetabulum during the reaming procedure. However, each time a larger reaming head is needed, the reamer must be removed from the patient, a larger reamer head is installed, and reinserted into position for further reaming. This procedure may be repeated several times until the acetabulum is completely prepared to fit the socket prosthetic. However, the need for continued removal, change, and reinsertion of the reamer increases the time required to perform the operation, resulting in increased infection exposure.

Expandable head acetabular reamers, such as the reamer disclosed in U.S. Pat. No. 3,702,611, are known in the art. While such expandable head reamers appear to mitigate the problem of having to constantly change reamer heads during a reaming procedure, they are mechanically complex and, due to the hemispherical head configuration of prior art reamers, may require a relatively large incision to introduce the tool reaming head into the patient, resulting in longer healing times and increased risk of infection.

Accordingly, an improved acetabular reamer is needed.

SUMMARY OF THE INVENTION

An acetabular reamer is described herein as including a reaming head having a number of arcuately-shaped segments, generally symmetrically distributed about a center point. In a further aspect, the segments of the acetabular reamer are extendable or retractable about the center point to create a variable dimensioned recess in an acetabular region. Each segment of the acetabular reamer may also include a convex cutting surface.

The acetabular reamer may also include a number of translating mechanisms, wherein each mechanism is coupled to a respective segment for providing translational movement of the segment. In addition, the reamer may include a transmission, mechanically coupled to each of the translating mechanisms, for transferring a rotational movement. The acetabular reamer may also include an adjustment rod for applying rotational movement to the transmission, and an adjustment handle, coupled to the adjustment rod, for applying the rotational movement to the adjustment rod. The acetabular reamer may further include a drive shaft adapted to receive a rotational driver for transferring rotational movement to the reaming head for reaming the acetabular region.

BRIEF DESCRIPTION OF THE DRAWINGS

The features and advantages of the present invention will become apparent from the following detailed description of the invention when read with the accompanying drawings in which.

DETAILED DESCRIPTION OF THE INVENTION

Figure 1:
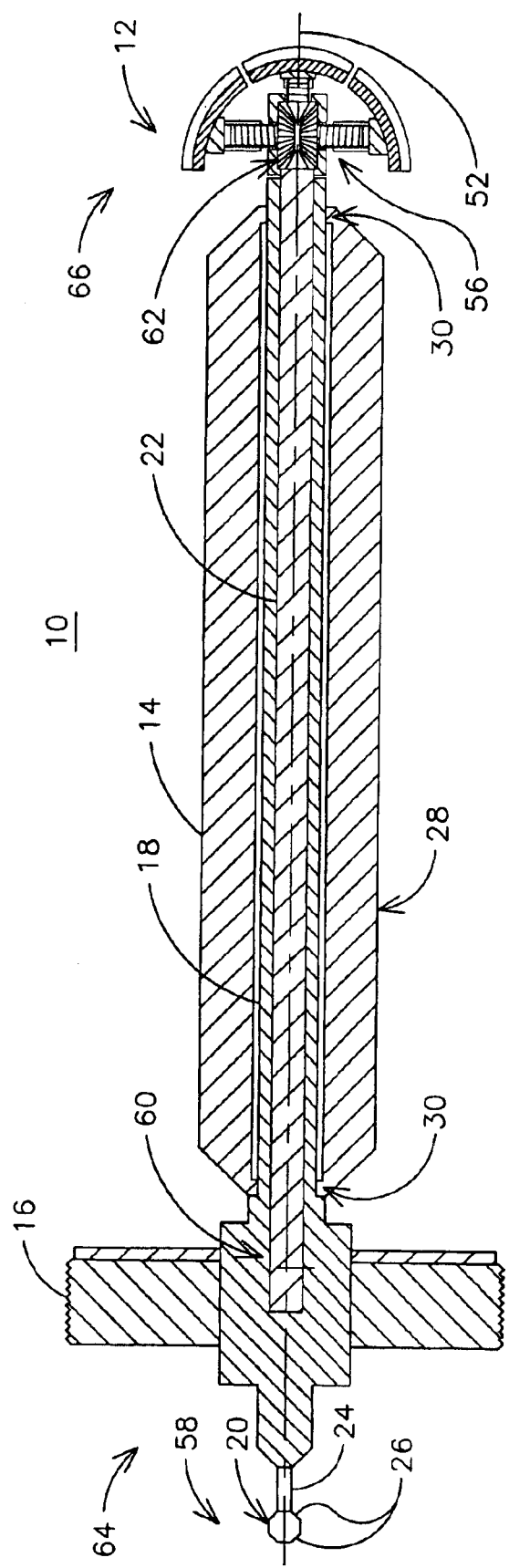
FIG. 1 is a cross-sectional top view of an acetabular reamer according to the present invention.

FIG. 1 is a cross-sectional top view of an acetabular reamer according to the present invention. Generally, the acetabular reamer includes a reaming head 12, a sleeve 14, an adjustment handle 16, a drive shaft 18 having a driving end 56 and a driven end 58, and an adjustment rod 22 having a handle end 60 and a geared end 62. In an aspect of the invention, the drive shaft 18 is adapted to receive a rotational driver such as a surgical drill (not shown) at the driven end 58 for providing rotational movement to the drive shaft 18. For example, the driven end 58 of the drive shaft 18 may be shaped to accommodate a chuck in a surgical drill so that the acetabular reamer 10 can be driven at various angles with respect to a centerline 52, thereby allowing flexibility and positioning when driving the reamer 10. Accordingly, the drive shaft 18 may be machined to include a waist 24 and a ball-like drive coupler 20 with chamfered edges 26 for allowing angular movement of the surgical drill with respect to the centerline 52 of the drive shaft 18.

A rotational movement applied to the drive shaft 18 at the driven end 58 transfers the rotational movement to the reaming head 12 at a reaming end 66 of the acetabular reamer 10 for performing a reaming procedure in the acetabular region. A sleeve 14 is slidingly positioned over the drive shaft 18 so that the sleeve 14 freely spins over the drive shaft 18, allowing an operator to hold the reamer 10 without interfering with rotation of the drive shaft 18. For example, the sleeve may be ergonomically shaped and textured with an exterior surface 28 for ease of positioning and holding the reamer 10 during a reaming procedure. As understood by one skilled in the art, an inside diameter of the sleeve 14 may be sized to be slightly larger than the outside diameter of the drive shaft 18, thus allowing free rotation of the handle about the drive shaft 18. In another aspect of the invention, bearing collars 30 may be included for providing friction-reduced rotation of the sleeve 14 about the drive shaft 18.

Figure 2:
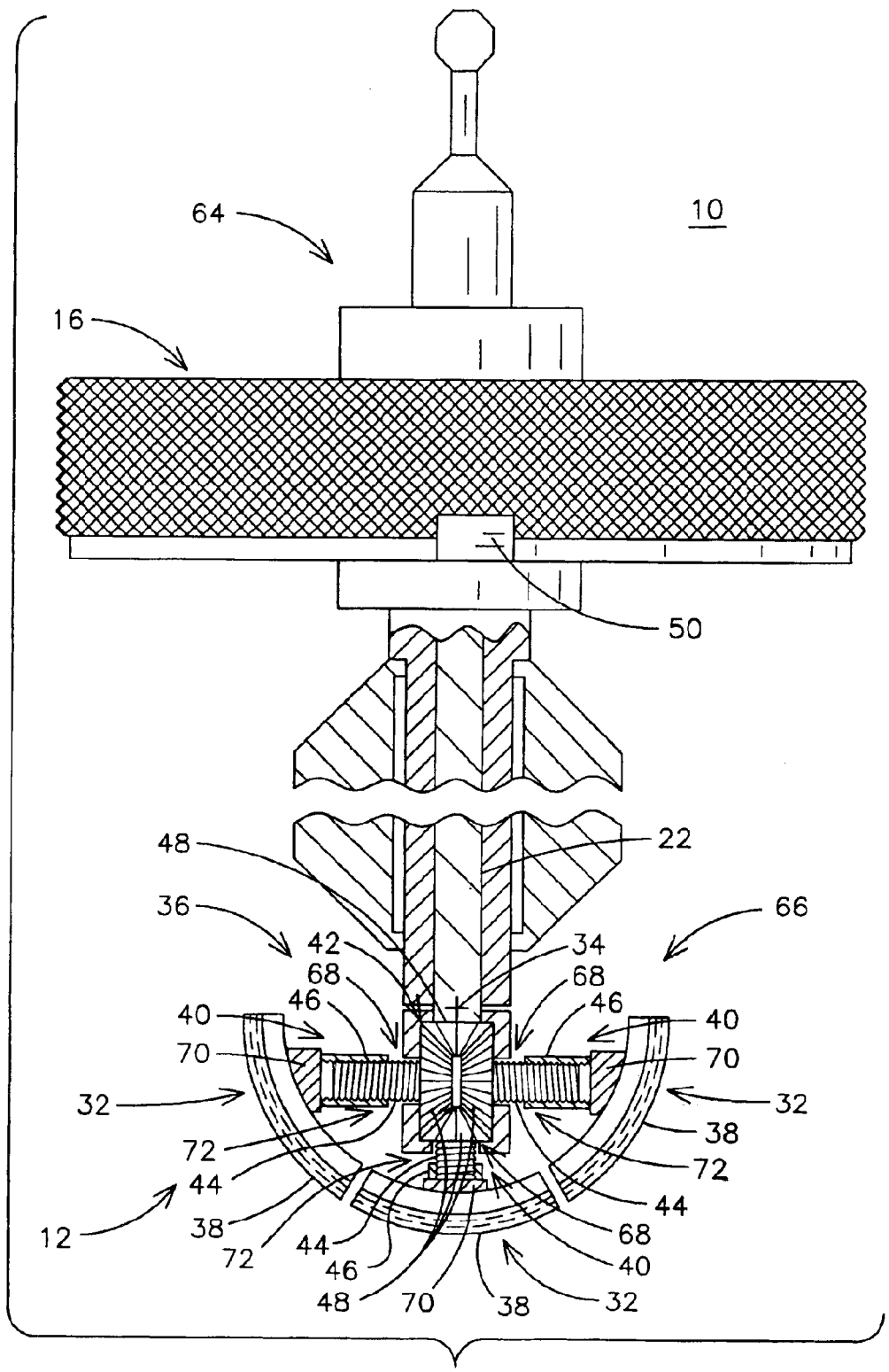
FIG. 2 is a partial, cross-sectional view showing a reaming end and an operator end of the acetabular reamer of FIG. 1.

FIG. 2 is a partial cross-sectional view showing the reaming end 66 and an operator end 64 of the acetabular reamer 10 of FIG. 1. The inventor of the present invention has innovatively realized that cutting a generally concave, hemispherical shape in an acetabular region does not necessarily require a hemispherically shaped reamer as used in the prior art. Accordingly, the inventor has created a novel adjustable, arcuate-shaped reaming head 12 that is only an arcuate-shaped portion of a hemisphere and can be inserted in a smaller incision than required when using prior art hemispherically shaped reamers. The reaming head 12 includes a plurality of arcuately shaped segments 32 generally symmetrically distributed about a center point 34. The segments 32 are extendible or retractable about the center point 34 to allow creating a variable dimension recess in an acetabular region.

Figure 4:
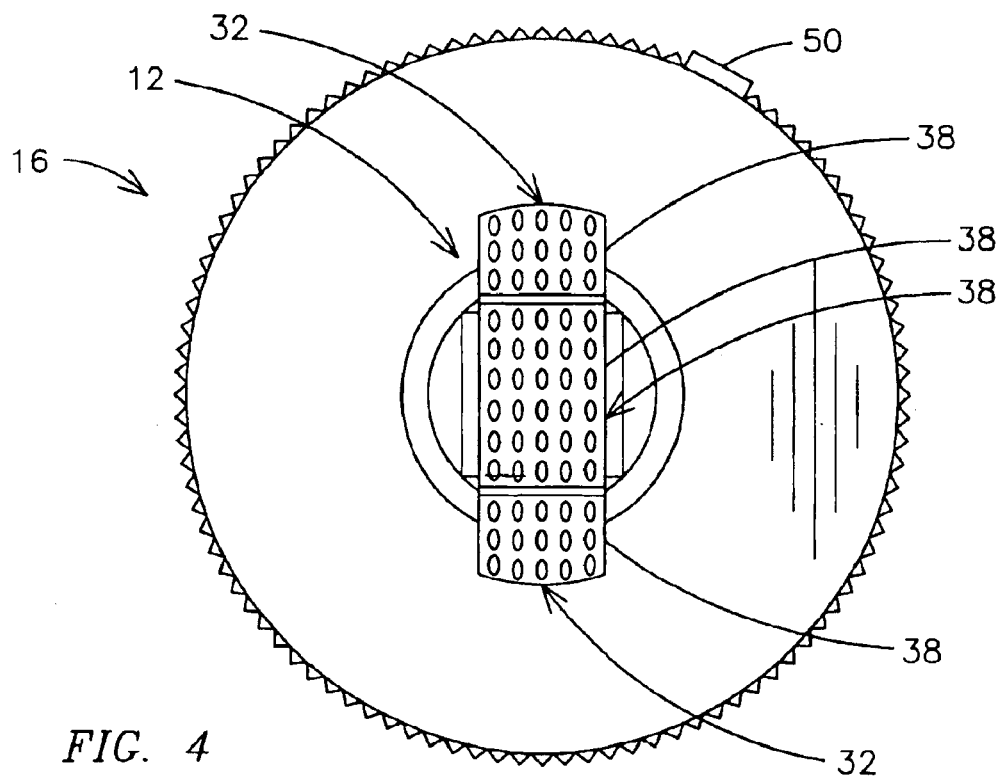
FIG. 4 is a reaming end view of the acetabular reamer of FIG. 1.

In an aspect of the invention, extension or retraction of the segments 32 is accomplished by an actuator 36 allowing an operator to adjust the size of the recess in the acetabular region as the reaming process progresses. The actuator 36 may be configured so that the segments 32 are uniformly extended or retracted such that the segments 32 remain generally symmetrically distributed about the center point 34. The segments 32 may be arranged to form an adjustable cutting arc subtending an angle of approximately 180° about the center point. Each segment 36 may further include a convex cutting surface 38 for cutting and removing bone material from the acetabular region during a reaming procedure. For example, each cutting surface may be configured to have a shape corresponding to a portion of a surface of a hemisphere subtending an arc of about 60 degrees with respect to the center point, so that all the segments 32 of the reaming head 12 align in an arc to form a section of a hemisphere subtending an angle of about 180 degrees. As shown in the distal end view of FIG. 4, the segments 32 generally can be configured in a narrow symmetrical "slice" of a hemispherical surface that advantageously provides an adjustable hemispherically shaped cutting arc, unlike prior art adjustable reamers that comprise a complete hemispherically shaped head. Accordingly, because the segments 32 of the reaming head 12 form only a portion of a hemisphere, the reamer head 12 can be inserted into the patient through a smaller incision than required with conventional hemispherically shaped reamers.

The cutting surfaces 38 may further comprise a plurality of cupped cutters distributed along the cutting surface 38 and oriented to face a rotational cutting direction, as is known in the art. In another form, the cutting surface 38 may comprise a plurality of grating holes, for example, having a raised, sharpened edge on one side of the hole facing the cutting direction for cutting and removal of bone in the acetabular region. The actuator 36 is attached to the segments 32 on a side opposite the cutting surface 38 and generally provides translational movement for extending and retracting the segments 32 to form a recess in acetabular region having a desired dimension, such as a hemispherical, concave shape sized to receive a prosthetic hip socket (not shown). In one form, the actuator 36 includes a number of translating mechanisms 40, a transmission 42 and an adjustment rod 22. Each segment 32 is attached to a translating mechanism 40 at a distal end so that the translating mechanism 40 provides translational movement of the respective segment 32. Each of the translating mechanisms 40 is connected to the transmission 42 at a rotation end 68 for transferring a rotational movement to each of the respective segments 32. An adjustment rod 44 mounted within the drive shaft 18 is coupled to the transmission 42 for applying the rotational movement to the transmission 42.

In an aspect of the invention, each translating mechanism 40 comprises a screw 44 and a threaded sleeve 46 for providing the desired translational movement of the segment 32. For example, the threaded sleeve 46 may be attached to the segment 32 at a segment mounting end 70, and have an opening at a screw receiving end 72 for receiving and engaging the screw 44 coupled to the transmission 42. Accordingly, as is understood in the art, rotational movement of the screw 44 provided by the transmission 42 is converted into a translational movement of the segment 32 by the action of the threaded sleeve 46 moving in relation to the screw 44. The pitch of the screw 44 and the thread sleeve 46 can be adjusted for each of the translating mechanisms, so that each segment 32 remains generally symmetrically distributed about the center point as the segments 32 are extended or retracted. For example, a right hand or left hand pitched thread may be used depending on the orientation of the rotational movement provided by a respective transmission element coupled to the translating mechanism 40. In addition, the number of threads per inch may be configured to provide a desired translational movement distance for a given rotational movement of the screw 44.

In another aspect of the invention, the transmission 42 may include a plurality of beveled gears 48 for imparting rotational movement to the translating mechanisms 40. One of the gears 48 may be coupled to the adjustment rod 22 to transfer a rotational movement of the adjustment rod 22 to the other gears 48 in the transmission 42. The adjustment rod 22 is attached to an adjustment handle 16 for applying a rotational movement to the adjustment rod 22 to allow the user to adjust the extension or retraction of the segments 32 coupled to the adjustment handle 22 through the respective translating mechanisms 40, the transmission 42 and the adjustment rod 22. Accordingly, a rotational movement of the adjustment handle 16 is transferred to the gears 48 in the transmission 42 and thereby to the screws 44 causing the threaded sleeves 46 of the translation mechanism 40 to translate the sleeves 46 and the attached segments 32 to expand or retract the segments 32 of the reamer head 12 corresponding to the direction of rotation of the adjustment handle 16. For example, the transmission 42 may be geared and the threads on the screws 44 and sleeves 46 may be pitched so that a counterclockwise rotation of the adjustment handle 12 causes the segments 32 to expand. Alternatively, a clockwise rotational movement applied to the adjustment handle 12 may cause the segments 32 to retract.

In yet another aspect of the invention, the handle 16 may be configured to expand or retract the segments 32 incrementally. For example, a spring loaded detent mechanism, as known in the mechanical arts, may be provided at the handle end 60 of the adjustment rod 22 to allow the adjustment handle 16 to be rotated a predetermined distance and then positively engage to limit further rotation of the adjustment handle 16 when the predetermined adjustment distance has been reached. The spring-loaded detent mechanism may comprise a spring-loaded key that mates with spaced apart engagement slots or grooves. Spacing or sizing of the slots or grooves can be selected so that the allowed rotation of the handle 16 causes the segments to extend or retract predetermined distances, thereby providing a predetermined radius of cut, or whatever degree of adjustment is necessary. In addition, a locking mechanism 50 can be provided to selectively secure the rotation of the actuator 36 to the drive shaft 18 when the extension or retraction of the segments 32 is not being adjusted, and the reamer 10 is being used to ream the acetabular region.

Figure 3:
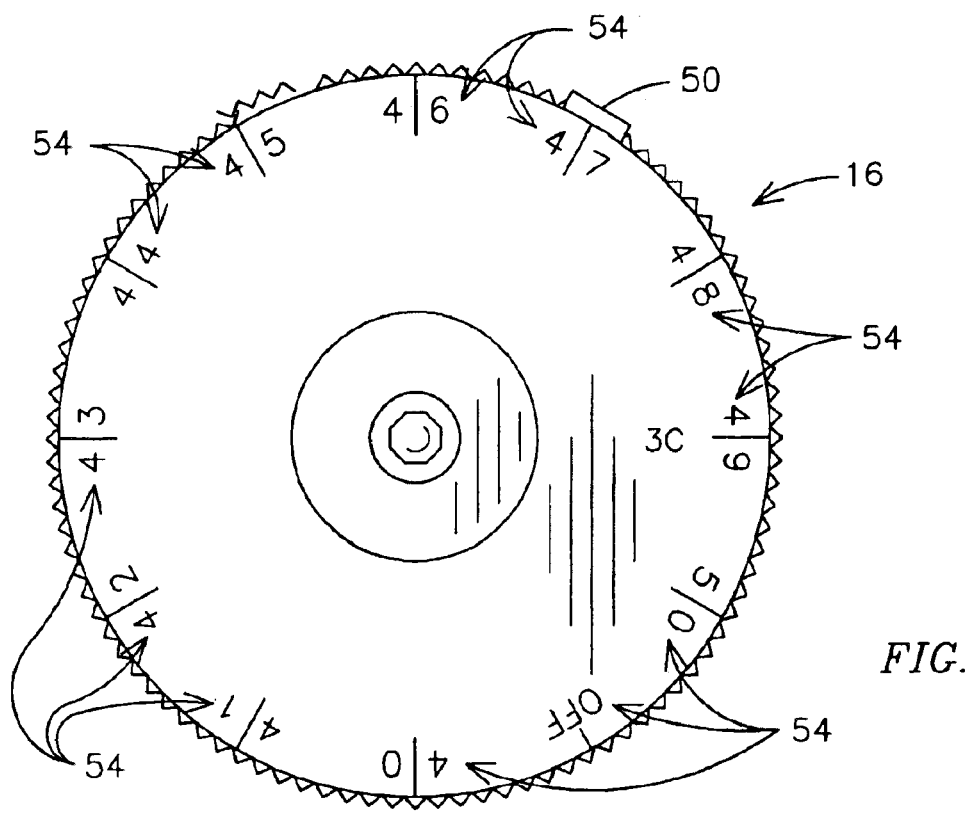
FIG. 3 is an operator end view of the acetabular reamer of FIG. 1.

As shown in the proximal end view of FIG. 3, the adjustment handle 16 may include indicia 54 corresponding to detent positions for adjusting the size of an acetabular reaming cut. Accordingly, a user can release the locking mechanism 50, adjust the adjustment handle 16 to a desired position, re-engage the locking mechanism 50, and continue reaming the acetabular region.

While the invention has been described in what is presently considered to be a preferred embodiment, various modifications and variations will become apparent to those skilled in the art. It is intended therefore that the invention not be limited to the specific disclosed embodiment but be interpreted within the full spirit and scope of the appended claims.

What is claimed is:

1. An acetabular reamer comprising a reaming head comprising a plurality of arcuately-shaped segments, the plurality of segments being generally symmetrically distributed about a center point, and being extendable or retractable about the center point to create a variable dimensioned recess in an acetabular region;

further comprising an actuator for selectively extending or retracting the segments so that the segments remain generally symmetrically distributed about the center point as the segments are expanded or retracted;

wherein the actuator further comprises;

a plurality of translating mechanisms, each mechanism having a first end and second end, the first end attached to a respective segment on a side opposite a convex surface of the segment, each translating mechanism providing translational movement of the respective segment;

a transmission, mechanically coupled to each of the translating mechanisms at the second end, for transferring a rotational movement to the translating mechanism;

an adjustment rod for applying the rotational movement to the transmission;

wherein the translating mechanism further comprises;

a screw coupled to the transmission for transferring the rotational movement; and a threaded sleeve, having a first sleeve end for attaching the segment and a second sleeve end for receiving the screw, the threaded sleeve being engaged with the screw for converting the rotational movement to a translational movement of the segment.

2. The reamer of claim 1 wherein the actuator further comprises an adjustment handle, coupled to an adjustment rod, for applying a rotational movement to the adjustment rod so that the respective segments synchronously move a predetermined translation distance such that the segments remain generally symmetrically distributed about the center point when a rotational movement is applied to the adjustment handle.

3. The reamer of claim 2 wherein the adjustment handle further comprises a locking mechanism for selectively locking the adjustment handle in incremental positions corresponding to incremental translation distances of the segments.

4. The reamer of claim 3 wherein the incremental translation distances are 1 millimeter (0.04 inch) increments.

5. The reamer of claim 1 wherein the plurality of segments form an arc subtending an angle of approximately 180 degrees about the center point.

6. The reamer of claim 1 wherein each segment further primes a convex cutting surface.

7. The reamer of claim 6 wherein the convex cutting surface further comprises a cupped configuration for cutting and scooping bone material away from the acetabular region.

8. The reamer of claim 6 wherein the convex cutting surface further comprises a grating hole configuration for cutting bone material away from the acetabular region.

9. The reamer of claim 1, further comprising a drive shaft having a driving end and a driven end, the reaming head attached to driving end and the driven end adapted to receive a rotational driver, the drive shaft transferring rotational movement to the reaming head for reaming the acetabular region.

10. The reamer of claim 9, further comprising a freely spinning sleeve, slidingly positioned over the drive shaft for allowing an operator to hold the reamer without interfering with a rotation of the drive shaft.

11. An acetabular reamer comprising:

a reaming head comprising a plurality of arcuately-shaped segments, the plurality of segments generally symmetrically distributed about a center point, the plurality of segments extendable or retractable about the center point to create a variable dimensioned recess in an acetabular region, each segment further comprising a convex cutting surface;

a plurality of translating mechanisms, each mechanism having a first end and second end, the first end attached to a respective segment on a side opposite the convex surface of the segment, each translating mechanism providing translational movement of the respective segment;

a transmission, mechanically coupled to each of the translating mechanisms at the second end, for transferring a rotational movement to the translating mechanism; and an adjustment rod for applying the rotational movement to the transmission;

an adjustment handle, coupled to the adjustment rod, for applying the rotational movement to the adjustment rod so that the respective segments synchronously move a predetermined translation distance such that the segments remain uniformly aligned in a desired cutting arc, when a rotational movement is applied to the adjustment handle;

a drive shaft having a driven end and a driving end, the reaming head attached to driving end and the driven end adapted to receive a rotational driver, the drive shaft transferring rotational movement to the reaming head for reaming the acetabular region; and a freely spinning sleeve, slidingly positioned over the drive shaft for allowing an operator to hold the reamer without interfering with a rotation of the drive shaft.

* * * * *